(12) United States Patent
Yuan et al.

(10) Patent No.: US 12,115,585 B2
(45) Date of Patent: Oct. 15, 2024

(54) FIBER CLOTH HAVING FUNCTIONAL COMPOSITE PARTICLES AND PREPARATION METHOD THEREFOR

(71) Applicants: NAXAU NEW MATERIALS CO., LTD., Jiaxing (CN); AODOZ MEDICAL TECHNOLOGY CORPORATION, Jiaxing (CN)

(72) Inventors: Ansu Yuan, Jiaxing (CN); Zhenwei Wen, Jiaxing (CN)

(73) Assignee: NAXAU NEW MATERIAL (ZHEJIANG) CO., LTD., Zhejiang (CN)

( * ) Notice: Subject to any disclaimer, the term of this patent is extended or adjusted under 35 U.S.C. 154(b) by 0 days.

(21) Appl. No.: 16/628,088

(22) PCT Filed: Jul. 18, 2018

(86) PCT No.: PCT/CN2018/096183
§ 371 (c)(1),
(2) Date: Jan. 2, 2020

(87) PCT Pub. No.: WO2019/015621
PCT Pub. Date: Jan. 24, 2019

(65) Prior Publication Data
US 2021/0156081 A1 May 27, 2021

(30) Foreign Application Priority Data

Jul. 18, 2017 (WO) ............... PCT/CN2017/093391

(51) Int. Cl.
| | |
|---|---|
| *B22F 9/12* | (2006.01) |
| *A61L 27/30* | (2006.01) |
| *B22F 1/05* | (2022.01) |
| *B22F 1/054* | (2022.01) |
| *B22F 1/145* | (2022.01) |

(Continued)

(52) U.S. Cl.
CPC ............... *B22F 9/12* (2013.01); *B22F 1/054* (2022.01); *B22F 1/145* (2022.01); *B22F 1/16* (2022.01); *C23C 14/0641* (2013.01); *C23C 14/08* (2013.01); *C23C 14/14* (2013.01); *C23C 14/16* (2013.01); *C23C 14/223* (2013.01); *C23C 14/325* (2013.01); *D06M 11/32* (2013.01); *D06M 11/58* (2013.01); *D06M 11/83* (2013.01); *D06M 16/00* (2013.01); *D06M 23/08* (2013.01); *D06M 23/12* (2013.01); *A61L 27/306* (2013.01); *B22F 1/056* (2022.01); *B22F 2201/20* (2013.01); *B22F 2301/10* (2013.01); *B22F 2301/255* (2013.01); *B22F 2302/20* (2013.01); *B22F 2302/25* (2013.01); *B22F 2304/00* (2013.01); *D06M 2101/04* (2013.01); *D06M 2101/16* (2013.01); *D06M 2200/00* (2013.01)

(58) Field of Classification Search
CPC .... B22F 9/12; B22F 1/145; B22F 1/16; B22F 1/054; B22F 1/056; C23C 14/0641; C23C 14/08; C23C 14/14; C23C 14/16; C23C 14/223; C23C 14/325; D06M 11/32; D06M 11/58; D06M 11/63; D06M 16/00; D06M 23/08; D06M 23/12; D06M 11/83; A61L 27/306
See application file for complete search history.

(56) References Cited

U.S. PATENT DOCUMENTS

| | | | | |
|---|---|---|---|---|
| 4,851,095 | A | * | 7/1989 | Scobey ................... C23C 14/56 204/192.15 |
| 2003/0124259 | A1 | * | 7/2003 | Kodas .............. H01C 17/06573 257/E21.174 |
| 2010/0040659 | A1 | | 2/2010 | Fahland et al. |

FOREIGN PATENT DOCUMENTS

| | | |
|---|---|---|
| CN | 1082625 A | 2/1994 |
| CN | 101054659 A | 10/2007 |

(Continued)

OTHER PUBLICATIONS

Extended European Search Report mailed Dec. 18, 2020 in counterpart European application EP 18 83 4856.9, 7 pages.

(Continued)

*Primary Examiner* — Amina S Khan
(74) *Attorney, Agent, or Firm* — Juan Carlos A. Marquez; Marquez IP Law Office, PLLC

(57) ABSTRACT

The present application relates to fiber cloth having functional composite particles and a preparation method therefor. The preparation method comprises: placing a solid metal block consisting of functional metal particles into a crucible using an evaporation and condensation process, and heating and evaporating the same into a vacuum physical vapor deposition (PVD) process furnace for condensation; depositing PVD ceramic layers on the outer surfaces of the functional metal particles under the condensed state using a PVD process to form the functional composite particles; and screening the functional composite particles by means of a particle filter and accelerating the particles to bombard the fiber cloth, thereby implanting the functional composite particles into the fiber cloth to form the fiber cloth having the functional composite particles. The functional composite particles in the present application can reduce contact between the internal functional metal particles and external oxygen, slowly release ionic metal ions of the functional metal particles, and prolong the action time of the functional metal particles. According to the present application, by implanting the functional composite particles into the fiber cloth, the fiber cloth with a long lasting antibacterial effect can be obtained.

9 Claims, 2 Drawing Sheets

(51) Int. Cl.
*B22F 1/16* (2022.01)
*C23C 14/06* (2006.01)
*C23C 14/08* (2006.01)
*C23C 14/14* (2006.01)
*C23C 14/16* (2006.01)
*C23C 14/22* (2006.01)
*C23C 14/32* (2006.01)
*D06M 11/32* (2006.01)
*D06M 11/58* (2006.01)
*D06M 11/83* (2006.01)
*D06M 16/00* (2006.01)
*D06M 23/08* (2006.01)
*D06M 23/12* (2006.01)
*D06M 101/04* (2006.01)
*D06M 101/16* (2006.01)

(56) References Cited

FOREIGN PATENT DOCUMENTS

| | | | | |
|---|---|---|---|---|
| CN | 104494229 A | 4/2015 | | |
| CN | 105861988 A | 8/2016 | | |
| CN | 205522773 U | 8/2016 | | |
| DE | 102004050462 | * | 6/2005 | ............. A61L 15/45 |
| EP | 1231292 | * | 8/2002 | ............. C23C 14/56 |
| WO | WO93/23092 | * | 11/1993 | ............. A61L 29/00 |

OTHER PUBLICATIONS

"Antimicrobial activity of Ag surfaces sputtered by magnetron sputtering," Mei et al., Material Research Innovations (2014) vol. 18, pp. S4-875 to S4-878.

"Ionized vapor deposition of antimicrobial Ti—Cu films with controlled copper release," Stranak et al., Elsevier Thin Solid Films 550 (2014), pp. 389-394.

* cited by examiner

FIBER CLOTH HAVING FUNCTIONAL COMPOSITE PARTICLES AND PREPARATION METHOD THEREFOR

The present application claims priority as the US national stage of PCT Application No. PCT/CN2018/096183 filed Jul. 18, 2018, which claims priority under 35 U.S.C. § 120 as a continuation-in-part of PCT Application No. PCT/CN2017/093391 filed on Jul. 18, 2017, both of which are hereby incorporated by reference in their entireties.

BACKGROUND

1. Technical Field

The present application relates to the technical field of composite materials, and more particularly to fiber cloth having functional composite particles and a preparation method therefor.

2. Description of the Related Art

The following description and examples are not to be taken as the prior art by virtue of their inclusion in the present section.

In general, there are two technical solution for preparation methods of an antibacterial dry towel or fiber cloth: the first technical solution is that an antibacterial material is made into silk threads (silver threads or copper threads) and the silk threads are woven into the fiber cloth; and the second technical solution is that the antibacterial material is made into antibacterial particles and the surface of the fiber cloth is coated with the antibacterial particles through spraying, printing and dyeing or a physical vapor deposition (PVD) technology, so that the fiber cloth has an antibacterial function.

However, a disadvantage of the first technical solution is that it is expensive and the antibacterial effect on the surface of the fiber cloth is not uniform. In the second technical scheme, due to the fact that the surface of the fiber cloth is directly coated with the antibacterial particles, the antibacterial particles will be in direct contact with air for a long time, resulting in forming an oxide layer the surface. Therefore, the fiber cloth cannot maintain a long-lasting and long-acting antibacterial effect. In addition, when the antibacterial particles coating the surface of the fiber cloth encounter external forces such as cleaning and kneading, the antibacterial particles will fall off, so that the fiber cloth loses the antibacterial effect.

In view of this, there is room for improvement in the preparation method for the antibacterial dry towel or cloth.

SUMMARY OF THE APPLICATION

One embodiment of the present application is to provide fiber cloth having functional composite particles and a preparation method therefor in an attempt to solve at least one problem existing in the related art to at least some extent.

According to one aspect of the present application, the present application provides a method for preparing fiber cloth having functional composite particles, and the preparation method comprises the following steps: placing a solid metal block consisting of functional metal particles into a crucible using an evaporation and condensation process, and heating and evaporating the same into a vacuum physical vapor deposition (PVD) process furnace for condensation; then depositing PVD ceramic layers on the outer surfaces of the functional metal particles under the condensed state using a PVD process to form the functional composite particles; and finally screening the functional composite particles by means of a particle filter and accelerating the particles to bombard the fiber cloth, thereby implanting the functional composite particles into the fiber cloth.

In some embodiments, the particle filter comprises a magnetic field generating device, an electric field generating device and a baffle, wherein the direction of a magnetic field is substantially perpendicular to the direction of an electric field.

In some embodiments, the electric field generating device is an independent bias power supply having a power of about 5 Kw to about 30 Kw.

In some embodiments, the magnitude of the magnetic field is from about 5 mT to about 1000 mT.

In some embodiments, the magnitude of the electric field is from about 5 KV to about 60 KV.

In some embodiments, the fiber cloth moves at a linear speed of 10 m/min to 40 m/min in a direction substantially perpendicular to the bombardment direction of the functional composite particles.

In some embodiments, the particle size of the screened functional composite particles is from about 15 nm to about 500 nm, and the energy of the screened functional composite particles is within the range of about 5 KeV to about 60 KeV.

In some embodiments, the functional metal particles are antibacterial metal particles that are Ag metal particles, Zn metal particles, Cu metal particles or a mixture thereof.

In some embodiments, the PVD ceramic layer comprises a metal oxide or a metal nitride prepared from Zr, Ti, Al, V, Nb, Ta, Y, Fe, Cr, Mo and W or a combination thereof, or a mixture thereof.

In some embodiments, the PVD ceramic layer is a PVD ceramic layer comprising ZrN, TiN, AlTiN, $Al_2O_3$, $ZrO_2$, $TiO_2$, VN, NbN, TaN, YN, FeN, CrN, MoN, WN, $V_2O_5$, $Nb_2O_5$, $Ta_2O_5$, $Y_2O_3$, $Fe_2O_3$, $Cr_2O_3$, $MoO_2$ or $WO_2$.

In some embodiments, the material of the fiber cloth is selected from cotton, hemp, silk, artificial fibers and a combination thereof.

According to another aspect of the present application, the present application provides fiber cloth, wherein fibers of the fiber cloth have functional composite particles, the functional composite particles comprise inner cores and shell layers, the inner cores are composed of functional metal particles and have outer surfaces, the shell layers are PVD ceramic layers, the shell layers are attached to the outer surfaces of the inner cores, and the shell layers are each of a crystalline structure so as to allow the ionic state of the functional metal particles in the inner cores to be slowly released to the outside of the shell layers via crystal boundaries.

In some embodiments, the distribution density of the functional composite particles in the fiber cloth is from about $10^6$/cm$^2$ to about $10^8$/cm$^2$.

Additional aspects and advantages of the embodiments of the present application will be described or shown in the following description or interpreted by implementing the embodiments of the present application.

BRIEF DESCRIPTION OF THE DRAWINGS

The accompanying drawings required for describing the embodiments of the present application will be briefly described below. Obviously, the accompanying drawings described below only show some embodiments of the present application. For those skilled in the art, the drawings of other embodiments can still be obtained according to the structures illustrated in the drawings without any creative effort.

PREFERRED EMBODIMENT OF THE PRESENT APPLICATION

For better understanding of the spirit of the present application, the functional composite particle provided in the embodiments of the present application will be described in further detail below with reference to the accompanying drawings and specific embodiments. The advantages and features of the embodiments of the present application will become clearer from the following description and the appended claims.

As used in the present application, terms "approximately", "substantially", "essentially", and "about" are used for describing and explaining a small variation. When being used in combination with an event or circumstance, the term may refer to an example in which the event or circumstance occurs precisely, and an example in which the event or circumstance occurs approximately. For example, when being used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, if a difference between two values is less than or equal to ±10% of an average value of the value (for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%), it could be considered that the two values are "substantially" the same.

Figure 1:
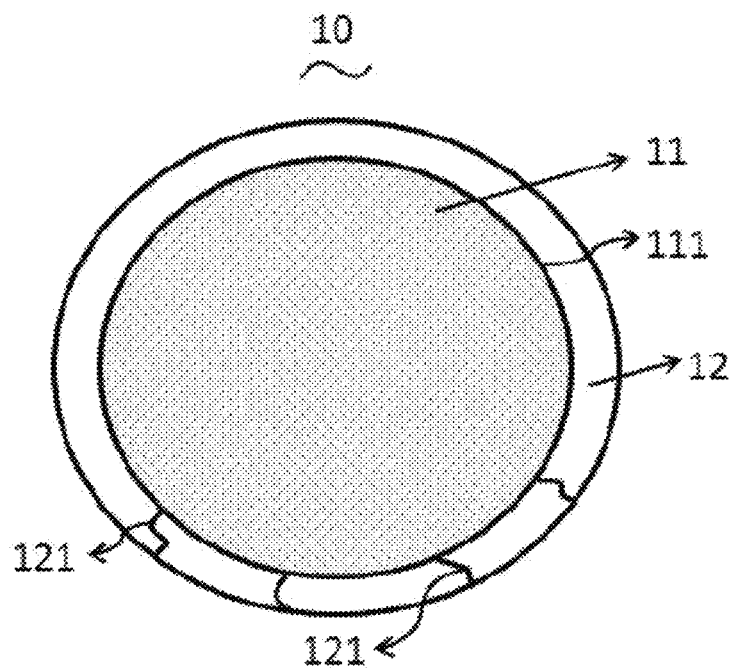
FIG. 1 is a schematic structural diagram of a functional composite particle according to one embodiment of the present application.
Figure 2:
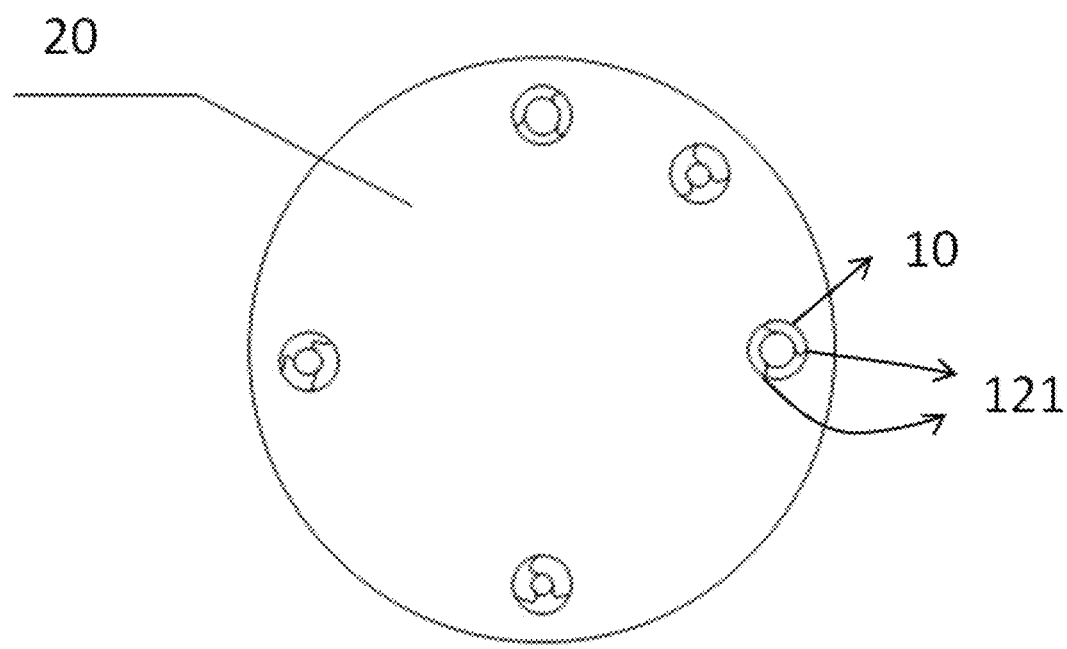
FIG. 2 is a schematic diagram of fiber cloth having functional composite particles according to one embodiment of the present application.
Figure 3:
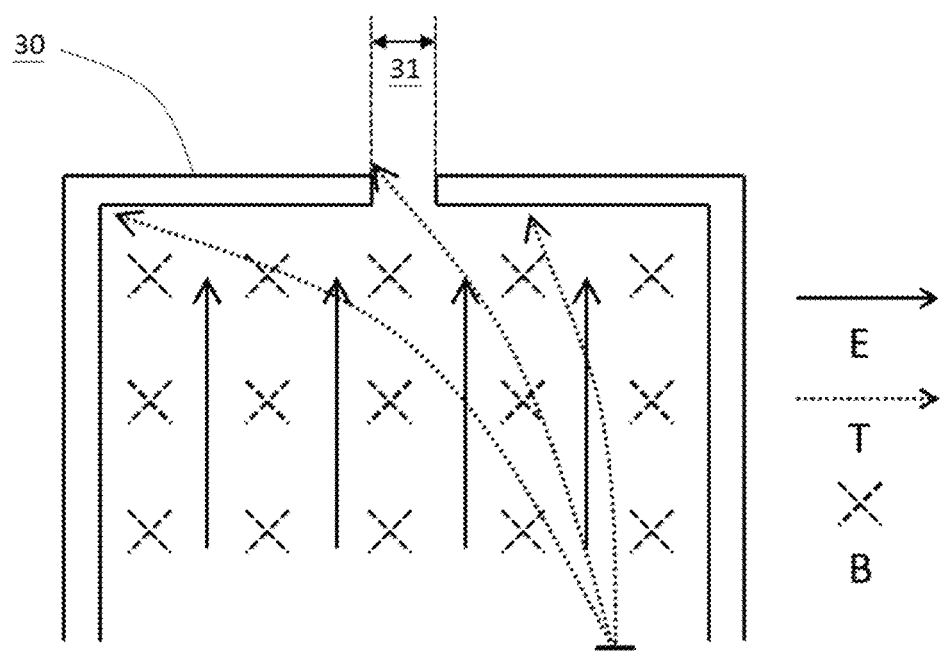
FIG. 3 is a schematic diagram of the functional composite particles passing through a particle filter according to one embodiment of the present application.

It should be noted that schematic diagrams in FIG. 1 to FIG. 3 are all in a very simplified form and are not drawn to accurate scale, but are merely used for convenience and clarity of description of the embodiments of the application.

FIG. 1 is a schematic structural diagram of a functional composite particle according to one embodiment of the present application. A functional composite particle 10 comprises an inner core 11 and a shell layer 12, wherein the inner core 11 is composed of a functional metal particle and has an outer surface 111. The shell layer 12 is attached to the outer surface 111 of the inner core 11 and is a physical vapor deposition (PVD) ceramic layer composed of ceramic materials.

FIG. 2 is a schematic diagram of fiber cloth having functional composite particles according to one embodiment of the present application. The functional composite particles 10 in the above embodiment are implanted into fibers of fiber cloth 20 using a charged particle injection method. From FIG. 1 and FIG. 2, the functional composite particles 10 are located in gaps and holes formed by fiber polymeric macromolecules in the fiber cloth 20, wherein the shell layers 12 of the functional composite particles are each of a crystalline structure and have crystal boundaries 121, and the crystal boundaries 121 provide channels to lead to the outer side of the shell layers 12 for the ionic state of functional metal particles in the inner cores 11. In one embodiment of the present application, in the use process of the functional composite particles 10, as the shell layers are each of the crystalline structure, the functional metal particles in the inner cores 11 may be slowly released to the outer side of the shell layers 12 in the form of the ionic state. In addition, the shell layers 12 wrapping the outer surfaces 111 of the inner cores 11 may effectively prevent the functional metal particles in the inner cores 11 from making contact with external oxygen and from being oxidized too early. By slowly releasing the functional metal particles in the form of the ionic state and reduce contact between the functional metal particles and external oxygen, the action time of the functional metal particles is prolonged, and accordingly the fiber cloth with a long lasting antibacterial effect may be obtained.

In order to obtain the fiber cloth having the functional composite particles, one embodiment of the present application provides a preparation method for the fiber cloth having the functional composite particles. The preparation method specifically comprises the following steps: firstly placing a solid metal block consisting of the functional metal particles into a crucible using an evaporation and condensation process, and heating and evaporating the same into a vacuum PVD process furnace for condensation so as to form inner cores 11; then depositing shell layers 12 made of ceramic materials on the outer surfaces 111 of the functional metal particles under the condensed state using a PVD process to form the functional composite particles 10; and consequently, screening the functional composite particles by means of a particle filter in the vacuum furnace and accelerating the functional composite particles to bombard the fiber cloth, thereby implanting the functional composite particles into the fiber cloth.

In one embodiment of the present application, the particle size of the condensed functional metal particles is affected by the heating power of a heating source.

In one embodiment of the present application, an electron gun is used as a heating source to heat the solid metal block consisting of the functional metal particles, and the current intensity range of the electron gun is from about 60 A to 300 A.

In one embodiment of the present application, the step of forming the PVD ceramic layers using the PVD process comprises the following substeps: introducing nitrogen or oxygen with the purity of about 99.999% into the vacuum PVD process furnace, opening a target containing biocompatible ceramic materials under a bias voltage of about 0 V to 1000 V, and depositing the PVD ceramic layers on the outer surfaces of the functional metal particles under the condensed state using the PVD process with an arc current of about 120 A to 200 A.

Embodiments of the present application may form the shell layers 12 by conventional PVD equipment using conventional PVD processes.

In one embodiment of the present application, the grain size range of the functional composite particles 10 is from about 15 nm to about 50000 nm. In one embodiment of the present application, the functional metal particles are antibacterial metal particles which comprise Ag metal particles, Cu metal particles, Zn metal particles or a mixture thereof. In one embodiment of the present application, the shell layers 12 are PVD ceramic layers comprising a metal oxide or a metal nitride prepared from Zr, Ti, Al, V, Nb, Ta, Y, Fe, Cr, Mo and W or a combination thereof, or a mixture thereof, the thickness of the shell layers is from about 5 nm to about 20000 nm, and the surface hardness is 1000 HV to 4500 HV, preferably 3000 HV to 4000 HV. In one embodiment of the present application, the shell layers 12 are PVD ceramic layers comprising ZrN, TiN, AlTiN, $Al_2O_3$, $ZrO_2$, $TiO_2$, VN, NbN, TaN, YN, FeN, CrN, MoN, WN, $V_2O_5$, $Nb_2O_5$, $Ta_2O_5$, $Y_2O_3$, $Fe_2O_3$, $Cr_2O_3$, $MoO_2$ or $WO_2$.

Specific embodiments of several functional composite particles 10 are illustrated in a PCT Patent Application with the Application Number of PCT/CN2017/093391, which is incorporated herein by reference in its entirety.

In one embodiment of the present application, the particle filter comprises a magnetic field generating device, an electric field generating device and a baffle, wherein the direction of a magnetic field is substantially perpendicular to the direction of an electric field.

FIG. 3 is a schematic diagram of the functional composite particles passing through a particle filter according to one embodiment of the present application. As shown in FIG. 3, in one embodiment of the present application, a particle filter 30 comprises a magnetic field generating device for generating a magnetic field B, an electric field generating device for generating an electric field E and a baffle having an opening 31. It will be clear to a person skilled in the art that, although the direction of the magnetic field B in FIG. 3 (the direction perpendicular into the paper plane) is perpendicular to the direction of the electric field E, in practice, a slight error in the included angle between the two directions may be tolerated and the included angle is not necessarily perfect 90 degrees. In addition, the magnetic field generating device for generating the magnetic field B comprises any device capable of generating the magnetic field, for example, the device may be, but is not limited to, a strong magnet or other electromagnetic device. The electric field generating device for the generating the electric field E comprises any device capable of generating the electric field E. In one embodiment of the present application, the electric field generating device may be, but is not limited to, an independent bias power supply having a power of about 5 Kw to about 30 Kw. In one embodiment of the present application, the magnitude of the magnetic field B is from about 5 mT to about 1000 mT. In one embodiment of the present application, the magnitude of the electric field is from about 5 KV to about 60 KV. In one embodiment of the present application, the magnetic field is a uniformly oriented magnetic field, and the electric field is a uniformly oriented electric field.

Since the functional composite particles have a small amount of electric charges after being formed, the functional composite particles may be accelerated to move in the direction of the electric field E when being injected into the particle filter 30; and at the same time, the magnetic field B provides a centripetal force (also referred to as Lorentz force) substantially perpendicular to the direction of movement of the functional composite particles, so that the trajectory of movement of the functional composite particles changes (as indicated by the dashed line T in FIG. 3).

The magnitude of the centripetal force F may be calculated by the following formula: $F=BQV=MV^2/R$ (1). It may be seen from the formula (1) that when the particle velocity V and the magnetic field B are both fixed by adjusting the electric field E and the magnetic field B, the movement radius R (namely, the movement trajectory) of the particles is proportional to the mass M (particle size) of the particles and inversely proportional to the charge Q carried by the particles. By providing the opening 31 substantially parallel to the direction of the magnetic field B on the baffle, the opening 31 may allow the functional composite particles having a specific movement trajectory to pass through the particle filter 30 and block other functional composite particles. Therefore, only the functional composite particles having the mass M (particle size) and the charge Q (energy) within a suitable range may pass through the particle filter.

In one embodiment of the present application, the opening size of the opening 31 is from about 1 cm to about 2 cm. In one embodiment of the present application, the particle size and energy of the particles passing through an accelerator may be adjusted by adjusting the values of the applied magnetic field B and the electric field E, and accordingly the screening of the functional composite particles is performed.

The fiber cloth having the functional composite particles and the preparation method therefor provided by the embodiment of the present application have the following characteristics and advantages:

Since the particle size of the fibers in general fiber cloth is within the range of about 10 μm to 100 μm, for example, the particle size of cotton cloth fibers is about 38 μm to 51 μm, the particle size of wool type fibers is about 64 μm to 114 μm, and the particle size of artificial fibers is about 30 μm to 50 μm, and the fibers in the fiber cloth are a mixture consisting of an ordered crystalline structure and a disordered amorphous structure. In the amorphous structure, the macromolecules of the fibers in the fiber cloth are disordered in arrangement, are loose in piling and have more gaps and holes. In one embodiment of the present application, the particle size of the functional composite particles screened and accelerated by the filter is from about 15 nm to about 500 nm and the energy is within the range of about 5 KeV to about 60 KeV by adjusting the strength of the electric field E and the magnetic field B in the particle filter, so that when the functional composite particles passing through the particle filter bombard the fiber cloth, the functional composite particles may penetrate through the surface barriers of the fiber macromolecules in the fiber cloth and pass through the gaps and holes of the amorphous structure in the fiber cloth, and accordingly the functional composite particles are implanted into the fiber cloth and are firmly embedded in the fibers after being subjected to a series of collision with the fiber macromolecules in the fiber cloth. In one embodiment of the present application, the particle size of the functional composite particles screened and accelerated by the filter is from about 15 nm to about 100 nm.

In one embodiment of the present application, after collision, most energy of the functional composite particles is converted into elastic potential energy and a small part of heat energy of the fibers, and since the particle size of the injected functional composite particles is far smaller than the particle size of the fibers of the fiber cloth, the elastic deformation caused by the functional composite particles is far smaller than the elastic limit of the fibers, and thus the physical properties of the fiber cloth are not changed.

In one embodiment of the present application, the injected particle flow density of the functional composite particles may be controlled by adjusting the power level of the electric field generating device, and the fiber cloth is set to move forwards at a specific speed, so that the density of the functional composite particles implanted in the fiber cloth per unit area is controlled. The density of the functional composite particles implanted into the fiber cloth per unit area is controlled within a reasonable range, so that the fiber cloth has an excellent antibacterial effect, and the fiber cloth cannot be softened and deformed due to excessive heat accumulation of the functional composite particles.

In one embodiment of the present application, the fiber cloth moves at a linear speed of 10 m/min to 40 m/min in the direction substantially perpendicular to the bombardment direction of the functional composite particles. In one embodiment of the present application, the distribution density of the functional composite particles in the fiber cloth is from about $10^6/cm^2$ to about $10^8/cm^2$.

In one embodiment of the present application, the functional composite particles may be implanted into the fiber cloth of any material, for example, the material of the fiber cloth may be, but is not limited to, one or more of cotton, hemp, silk and artificial fibers.

The preparation for the fiber cloth having the functional composite particles according to the present application will be further described with reference to specific preferred embodiments of the present application below.

Embodiment 1

Firstly, an Ag metal block was placed into a crucible, and heated using an electron gun at a current intensity of 100 A so as to be evaporated and kept condensed in a vacuum physical vapor deposition (PVD) process furnace, so that Ag metal particles under a condensed state were formed.

Then nitrogen with a purity of 99.999% was introduced into the vacuum PVD process furnace, a target containing Ti was opened under the condition that a bias voltage is 90 V, and TiN ceramic layers were deposited on the outer surfaces of the Ag metal particles under the condensed state using a PVD process with an arc current of 150 A, so that charged functional composite Ag particles were formed.

Then the charged functional composite Ag particles were guided into a particle filter, wherein the amplitude of a magnetic field of the particle filter was about 700 mT and the power of an independent bias power supply of the particle filter was 10 Kw so as to form an electric field of about 20 KV, such that the particle size of the functional composite Ag particles passing through the particle filter was from about 50 nm to about 70 nm, and the energy thereof was within the range of about 5 KeV to about 60 KeV. Fiber non-woven cloth of a cotton material was placed at an opening of the particle filter, the surface of the fiber non-woven cloth was made substantially perpendicular to the particle ejection direction, and the surface of the fiber non-woven cloth was made pass through the opening of the particle filter at a linear speed of 30 m/min, so that the functional composite Ag particles were uniformly driven onto the surface of the fiber non-woven cloth, and the fiber non-woven cloth having the functional composite Ag particles and with a particle distribution density of about $10^7/cm^2$ was obtained.

Embodiment 2

Firstly, a Cu metal block was placed into a crucible, and heated using an electron gun at a current intensity of 130 A so as to be evaporated and kept condensed in a vacuum physical vapor deposition (PVD) process furnace, so that Cu metal particles under a condensed state were formed.

Then nitrogen with a purity of 99.999% was introduced into the vacuum PVD process furnace, a target containing Ti was opened under the condition that a bias voltage was 120 V, and TiN ceramic layers were deposited on the outer surfaces of the Cu metal particles under the condensed state using a PVD process with an arc current of 150 A, so that charged functional composite Cu particles were formed.

Then the charged functional composite Cu particles were guided into a particle filter, wherein the amplitude of a magnetic field of the particle filter was about 400 mT and the power of an independent bias power supply of the particle filter was 15 Kw so as to form an electric field of about 13 KV, such that the particle size of the functional composite Cu particles passing through the particle filter was from about 45 nm to about 80 nm, and the energy thereof was within the range of about 5 KeV to about 60 KeV. Fiber non-woven cloth of a cotton material was placed at an opening of the particle filter, the surface of the fiber non-woven cloth was made substantially perpendicular to the particle ejection direction, and the surface of the fiber non-woven cloth was made pass through the opening of the particle filter at a linear speed of 30 m/min, so that the functional composite Cu particles were uniformly driven onto the surface of the fiber non-woven cloth, and the fiber non-woven cloth having the functional composite Cu particles and with a particle distribution density of about $10^7/cm^2$ was obtained.

Embodiment 3

Firstly, a Zn metal block was placed into a crucible, and heated using an electron gun at a current intensity of 80 A so as to be evaporated and kept condensed in a vacuum physical vapor deposition (PVD) process furnace, so that Zn metal particles under a condensed state were formed.

Then nitrogen with a purity of 99.999% was introduced into the vacuum PVD process furnace, a target containing Ti was opened under the condition that a bias voltage was 70 V, and TiN ceramic layers were deposited on the outer surfaces of the Zn metal particles under the condensed state using a PVD process with an arc current of 150 A, so that charged functional composite Zn particles were formed.

Then the charged functional composite Zn particles were guided into a particle filter, wherein the amplitude of a magnetic field of the particle filter was about 450 mT and the power of an independent bias power supply of the particle filter was 12 Kw so as to form an electric field of about 15 KV, such that the particle size of the functional composite Zn particles passing through the particle filter was from about 65 nm to about 90 nm, and the energy thereof was within the range of about 5 KeV to about 60 KeV. Fiber non-woven cloth of a cotton material was placed at an opening of the particle filter, the surface of the fiber non-woven cloth was made substantially perpendicular to the particle ejection direction, and the surface of the fiber non-woven cloth was made pass through the opening of the particle filter at a linear speed of 30 m/min, so that the functional composite Zn particles were uniformly driven onto the surface of the fiber non-woven cloth, and the fiber non-woven cloth having the functional composite Zn particles and with a particle distribution density of about $10^7/cm^2$ was obtained.

The above description summarizes the features of several embodiments, which enables those of ordinary skill in the art to understand the various aspects of the present application. Those of ordinary skill in the art can readily use the present application as a basis for designing or modifying other compositions to achieve the same objectives and/or the same advantages as the embodiments herein. It is also to be understood by those of ordinary skill in the art that these equal examples do not depart from the spirit and scope of the present application, and it is possible to make various changes, substitutions and modifications to the present application without departing from the spirit and scope of the present application. Although the methods disclosed herein have been described with reference to the specific operations that are performed in a specific order, it should be understood that these operations can be combined, subdivided, or reordered to form an equivalent method without departing from the teachings of the present application. Therefore, the order and grouping of operations are not a limitation to the present application unless specifically indicated herein.

What is claimed is:

1. A method for preparing fiber cloth having functional composite particles, comprising:

placing a solid metal block consisting of functional metal particles into a crucible using an evaporation and condensation process, and heating and evaporating the solid metal block in a vacuum physical vapor deposition (PVD) process furnace for condensation;

depositing PVD ceramic layers on the outer surfaces of the functional metal particles under the condensed state using a PVD process to form the functional composite particles; and screening the functional composite particles by means of a particle filter and accelerating the particles to bombard the fiber cloth, thereby implanting the functional composite particles into the fiber cloth;

wherein the particle filter comprises a magnetic field generating device, an electric field generating device and a baffle, and the direction of a magnetic field is substantially perpendicular to the direction of an electric field; and wherein the particle size of the screened functional composite particles is from about 15 nm to about 500 nm, and the energy of the screened functional composite particles is within the range of about 5 KeV to about 60 KeV.

2. The method according to claim 1, wherein the electric field generating device is an independent bias power supply having a power of about 5 Kw to about 30 Kw.

3. The method according to claim 1, wherein the magnitude of the magnetic field is from about 5 mT to about 1000 mT.

4. The method according to claim 1, wherein the magnitude of the electric field is from about 5 KV to about 60 KV.

5. The method according to claim 1, wherein the fiber cloth moves at a linear speed of 10 m/min to 40 m/min in a direction substantially perpendicular to the bombardment direction of the functional composite particles.

6. The method according to claim 1, wherein the functional metal particles are antibacterial metal particles that are selected from Ag metal particles, Zn metal particles, Cu metal particles or a mixture thereof.

7. The method according to claim 1, wherein the PVD ceramic layer comprises a metal oxide or a metal nitride prepared from Zr, Ti, Al, V, Nb, Ta, Y, Fe, Cr, Mo and W or a combination thereof.

8. The method according to claim 7, wherein the PVD ceramic layer is a PVD ceramic layer comprising ZrN, TiN, AlTiN, $Al_2O_3$, $ZrO_2$, $TiO_2$, VN, NbN, TaN, YN, FeN, CrN, MON, WN, $V_2O_5$, $Nb_2O_5$, $Ta_2O_5$, $Y_2O_3$, $Fe_2O_3$, $Cr_2O_3$, $MoO_2$ or $WO_2$.

9. The method according to claim 1, wherein the material of the fiber cloth is selected from cotton, hemp, silk, artificial fibers or a combination thereof.

* * * * *